US006369278B2

(12) United States Patent
Noritake et al.

(10) Patent No.: US 6,369,278 B2
(45) Date of Patent: Apr. 9, 2002

(54) PROCESS FOR PREPARING EXTRACT CONTAINING AT LEAST ONE HYDROPEROXIDE

(75) Inventors: Tomoyuki Noritake; Shigeru Goto, both of Ichihara; Kenji Itoh, Sodegaura, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/730,583

(22) Filed: Dec. 7, 2000

(30) Foreign Application Priority Data

Dec. 21, 1999 (JP) .......................................... 11-362403
Jan. 25, 2000 (JP) ....................................... 2000-016281

(51) Int. Cl.⁷ ............................................ C07C 409/00
(52) U.S. Cl. ...................... 568/576; 568/569; 568/568; 568/571
(58) Field of Search ................................ 568/576, 569, 568/568, 571

(56) References Cited

U.S. PATENT DOCUMENTS 5,959,155 A * 9/1999 Ohmae et al. .............. 568/576

* cited by examiner

Primary Examiner—Johann Richter
Assistant Examiner—J. Parsa
(74) Attorney, Agent, or Firm—Sughrue Mion, PLLC

(57) ABSTRACT

There are provided:

(I) a process for preparing an extract containing at least one hydroperoxide, which comprises the steps of:
 (1) oxidizing an aromatic hydrocarbon substituted with an alkyl group to obtain a liquid reaction mixture, and
 (2) extracting at least one hydroperoxide in the liquid reaction mixture to obtain an extract having a concentration of acetone of not more than 1% by weight: and (II) a process for preparing an extract containing at least one hydroperoxide, which comprises the steps of,
 (1) oxidizing an aromatic hydrocarbon substituted with an alkyl group to obtain a liquid reaction mixture, and
 (2) extracting at least one hydroperoxide with an aqueous alkali solution having an A value of not more than 10 to obtain an extract.

6 Claims, No Drawings

US 6,369,278 B2

PROCESS FOR PREPARING EXTRACT CONTAINING AT LEAST ONE HYDROPEROXIDE

FIELD OF THE INVENTION

The present invention relates to a process for preparing an extract containing at least one hydroperoxide. More specifically, the present invention relates to a process for preparing an extract containing at least one hydroperoxide, in which extract said hydroperoxide is prevented from decomposing undesirably.

BACKGROUND OF THE INVENTION

As a process for producing an object compound such as resorcinol using, as a starting material, an aromatic hydrocarbon substituted with an alkyl group such as 1,3-diisopropylbenzene, there is known a process comprising the steps of (i) to (v) as mentioned below:

(i) subjecting a liquid material containing an aromatic hydrocarbon substituted with an alkyl group to oxidation, thereby obtaining a liquid reaction mixture, (ii) extracting hydroperoxides in the liquid reaction mixture with an aqueous alkali solution, thereby obtaining an extract-1, (iii) extracting the hydroperoxides in the extract-1 with an organic solvent, thereby obtaining an extract-2, wherein the aqueous alkali solution separated in this step is recycled to the above-mentioned step (ii) or step (iii), (iv) subjecting the hydroperoxides in the extract-2 to acid decomposition, thereby obtaining a reaction mixture containing the object compound and a by-produced acetone, and (v) distilling the reaction mixture to separate the object compound and a low boiling point fraction such as the organic solvent used, wherein the organic solvent separated in this step is recycled to the above-mentioned step (iii).

However, the above-mentioned process comprising the recycling system has a problem that the desired hydroperoxides in the extract-1 are apt to decompose therein undesirably, when a concentration of acetone in the extract-1 obtained in the step (ii) is high, or when an A value of the aqueous alkaline solution used in the step (ii) is high, which A value is as defined below.

SUMMARY OF THE INVENTION

An object of the present invention is to provide a process for preparing an extract containing at least one hydroperoxide, according to which the hyroperoxide(s) in the extract-1 is(are) prevented from decomposing undesirably.

That is, the present invention provides a process for preparing an extract containing at least one hydroperoxide, which comprises the steps of:

(1) oxidizing an aromatic hydrocarbon substituted with an alkyl group to obtain a liquid reaction mixture, and (2) extracting at least one hydroperoxide with an aqueous alkali solution to obtain an extract having a concentration of acetone of not more than 1% by weight.

The present invention also provides a process for preparing an extract containing at least one hydroperoxide, which comprises the steps of, (1) oxidizing an aromatic hydrocarbon substituted with an alkyl group to obtain a liquid reaction mixture, and (2) extracting at least one hydroperoxide with an aqueous alkali solution having an A value of not more than 10 to obtain an extract, wherein the A value is a volume in terms of ml of the below-defined aqueous hydrochloric acid solution consumed between a first inflection point and a second inflection point in a pH titration curve obtained when 10 ml of the aqueous alkali solution is subjected to titration with a 1 N(normal) aqueous hydrochloric acid solution, provided that when the inflection point is not clear, or when there are three or more inflection points, the A value is a volume in terms of ml of said aqueous hydrochloric acid solution consumed during a pH transition of from 7 to 2 in the above-defined titration.

DETAILED DESCRIPTION OF THE INVENTION

The term, "aromatic hydrocarbon substituted with an alkyl group", means an aromatic hydrocarbon substituted with a primary, secondary or tertiary alkyl group having 1 to 10 carbon atoms. A number of the alkyl group appended to the aromatic hydrocarbon is not limited. Preferred number is 1 to 3. Examples of the alkyl group are methyl, ethyl and isopropyl groups, Of these, an ethyl group and secondary or tertiary alkyl groups such as an isopropyl group are preferred. Examples of the aromatic hydrocarbon substituted with the alkyl group are methylbenzene, ethylbenzene, isopropylbenzene, 1,3-diisopropylbenzene and 1-methyl-3-isopropylbenzene. Of these, ethylbenzene, isopropylbenzene, 1,3-diisopropylbenzene and 1-methyl-3-isopropylbenzene are preferred.

The term, "aqueous alkali solution", used in the present invention means an aqueous alkali solution having an A value of not more than 10, and preferably not more than 5. When said A value exceeds 10, it is difficult to prevent the hydroperoxide(s) in the extract from decomposing undesirably.

The process of the present invention is characterized by either obtaining the extract having a concentration of acetone of not more than 1% by weight, or using the aqueous alkali solution having an A value of not more than 10, whereby the hydroperoxide(s) in the extract can be prevented from decomposing undesirably.

The above-mentioned term, "A value", means a volume in terms of ml of the below-defined aqueous hydrochloric acid solution consumed between a first inflection point and a second inflection point in a pH titration curve obtained when 10 ml of the aqueous alkali solution Is subjected to titration with a 1 N(normal) aqueous hydrochloric acid solution, provided that when the inflection point is not clear, or when there are three or more inflection points, the A value is a volume in terms of ml of said aqueous hydrochloric acid solution consumed during a pH transition of from 7 to 2 in the above-defined titration.

The present invention is explained below with reference to an instance relating to a process for producing resorcinol, which is an object compound, from 1,3-diisorpopylbenzene as a starting material, which material is an aromatic hydrocarbon substituted with an alkyl group, wherein respective hydroperoxides are expressed by the following symbols. Incidentally, step (i) and step (ii) mentioned below are directly related to the present invention.

MHPO: 3-isopropyl-1-(2-hydroperoxy-2-propyl)benzene
DHPO: 1,3-di-(2-hydroperoxy-2-propyl)benzene
CHPO: 3-(2-hydroxy-2-propyl)-1-(2-hydroperoxy-2-propyl)benzene Step (i)

This step is to subject a liquid material containing 1,3-diisopropylbenzene to oxidation, thereby obtaining a liquid reaction mixture containing the hydroperoxides. A method of said oxidation is not limited, and, for example, a known method using oxygen or air can be applied therefor. The method can be carried out under usual oxidation conditions, such as a temperature of 70 to 110° C., a pressure of 0 to 1 MPa (G), and a residence time of 0 to 50 hours. As a reactor, for example, a flow type reaction vessel or reaction column can be used. Since it is usual to carry out the process for producing resorcinol from 1,3-diisopropylbenzene in a continuous manner, and therefore the liquid material contains a recycled liquid containing at least one hydroperoxide and unreacted 1,3-diisopropylbenzene, the usual liquid material has the following main components (a weight of the liquid material is 100% by weight).

| 1,3-Diisopropylbenzene: | 10 to 40% by weight |
|---|---|
| MHPO: | 20 to 60% by weight |
| DHPO: | 0 to 5% by weight |
| CHPO: | 0 to 10% by weight |

The usual liquid reaction mixture obtained has the following main components (a weight of the liquid reaction mixture is 100% by weight).

| 1,3-Diisopropylbenzene: | 10 to 40% by weight |
|---|---|
| MHPO: | 20 to 60% by weight |
| DHPO: | 3 to 30% by weight |
| CHPO: | 0 to 10% by weight |

Step (ii)

This step is to extract at least one hydroperoxide present in the liquid reaction mixture obtained in the above step (i) with an aqueous alkali solution, thereby obtaining an extract-1 containing mainly DHPO and CHPO. A weight ratio of the aqueous alkali solution to the liquid reaction mixture (aqueous alkali solution/liquid reaction mixture) is usually from 0.2 to 5. As the alkali, sodium hydroxide is preferred from an economical point of view. A concentration of the alkali in the aqueous alkali solution is usually from 0.1 to 30% by weight. The extraction can be carried out, for example, under usual conditions such as a temperature of 0 to 70° C. in a manner of 1- to 10-stage countercurrent extraction. As an extractor, for example, a mixer settler and an extraction column can be used.

Step (iii)

This step is to extract at least one hydroperoxide in the extract-1 obtained in the above step (ii) with an organic solvent, thereby obtaining an extract-2 containing the desired hydroperoxide(s). In this step, it is usual that DHPO and CHPO are predominantly distributed to the organic solvent by the difference in each distribution coefficient of DHPO and CHPO to the aqueous alkali solution and the organic solvent. A weight ratio of the aqueous alkali solution to the organic solvent (aqueous alkali solution/organic solvent) is usually from 0.2 to 10. It is recommendable to use methyl isobutyl ketone as the organic solvent. An extraction temperature is usually from 20 to 80° C. As an extractor, for example, a mixer settler and an extraction column can be used. The aqueous alkali solution separated from the organic solvent is generally recycled to step (ii) or step (iii). Here, if desired, the aqueous alkali solution separated from the organic solvent may be subjected to, for example, purging, whereby the concentration of acetone in the extract-1 obtained in step (ii) can be kept within the range as defined above, and the A value of the extract-1 used in the step (ii) can be also kept within the range as defined above.

Step (iv)

This step is to subject the above-mentioned extract-2 to acid decomposition, thereby obtaining a reaction mixture containing resorcinol. In this step, DHPO in the extract-2 decomposes into resorcinol and acetone through the acid decomposition, and CHPO in the extract-2 decomposes into 3-(2-propenyl)phenol and acetone through the acid decomposition.

Step (v)

This step is to distill the reaction mixture obtained in the above step (iv), thereby separating the object compound (resorcinol) from a low boiling point fraction such as acetone and the organic solvent. The organic solvent separated is generally recycled to step (iii). However, if desired, the organic solvent may be treated, for example, with an equipment such as a fractionator to separate acetone present therein, whereby the concentration of acetone in the aqueous alkali solution separated in step (iii) can be controlled to not more than 1% by weight, and as a result, the concentration of acetone in the extract-1 obtained in step (ii) can be kept within the range as defined above.

As clear from the above description, the extract containing at least one hydroperoxide, which extract is obtained according to the present invention, can be effectively used, for example, for the production of resorcinol, when the aromatic hydrocarbon substituted with an alkyl group is 1,3-diisopropylbenzene.

EXAMPLE

The present invention Is illustrated in more detail with reference to the following Examples, which are not limitative for the scope of the present invention.

Example 1

1,3-Diisopropylbenzene was oxidized with air to obtain a liquid reaction mixture. The liquid reaction mixture containing hydroperoxides was subjected to extraction with an aqueous alkali solution containing no acetone (concentration of sodium hydroxide=8% by weight), and further the resulting extract was washed with 1,3-diisopropylbenzene. The hydroperoxides in the washed extract were determined according to an iodometry method, and as a result, the concentration of the hydroperoxides was found to be about 10% by weight ($C_0$% by weight).

100 Grams of the above-mentioned washed extract was put in a 300 cc flask equipped with a condenser, and stirred at 60° C. The concentration ($C_2$% by weight) of the hydroperoxides after a 2-hour lapse of time from the start of stirring, the concentration ($C_4$% by weight) of the hydroperoxides after a 4-hour lapse of time therefrom, the concentration ($C_6$% by weight) of the hydroperoxides after a 6-hour lapse of time therefrom, and the concentration ($C_{10}$% by weight) of the hydroperoxides after a 10-hour lapse of time therefrom, were determined respectively. Here, respective concentrations of the hydroperoxides ($C_0$ and $C_2$ to $C_{10}$) were expressed in terms of 1,3-di-(2-hydroperoxy-2-propyl)benzene (DHPO).

A retention percent of the hydroperoxides after the fixed hour lapse of time was calculated by the following equation, and the results thereof are as shown in Table 1. The higher the retention percent, the more the prevention of undesired decomposition of the hydroperoxides during the alkali extraction step.

Retention percent after 2-hour lapse of time (%)  = 100 × $C_2/C_0$   (I)
Retention percent after 4-hour lapse of time (%)  = 100 × $C_4/C_0$   (II)
Retention percent after 6-hour lapse of time (%)  = 100 × $C_6/C_0$   (III)
Retention percent after 10-hour lapse of time (%) = 100 × $C_{10}/C_0$ (IV)

Examples 2 and 3 and Comparative Example 1 and 2

Acetone was added to 100 g of the washed extract obtained in Example 1 in each amount of 0.1 g (Example 2), 1 g (Example 3), 3 g (Comparative Example 1) and 10 g (Comparative Example 2), and then Example 1 was repeated to determine the retention percent. The results thereof are as shown in Table 1.

Example 4

1,3-Diisopropylbenzene was oxidized with air to obtain a liquid reaction mixture. 60 Grams of the liquid reaction mixture and 30 g of an aqueous alkali solution having the A value of 0 (concentration of sodium hydroxide=7% by weight) were put in a 200 cc flask equipped with a condenser, and stirred at 70° C. under nitrogen atmosphere. A concentration ($C_0$% by weight) of the hydroperoxides immediately after the start of stirring and that ($C_2$% by weight) after a 2-hour lapse of time were measured to calculate a retention percent according to the above equation (I). Here, respective concentrations of the hydroperoxides ($C_0$ and $C_2$) were expressed in terms of 1,3-di(2-hydroperoxy-2-propyl)benzene (DHPO). The results thereof are as shown in Table 2.

Example 5 and Comparative Example 3

Example 4 was repeated, except that respective aqueous sodium hydroxide solutions having the A values of 4.2 (Example 5) and 13.7 (Comparative Example 3) were used. The results thereof are as shown in Table 2.

TABLE 1

|  | Example | | | Comparative Example | |
| --- | --- | --- | --- | --- | --- |
|  | 1 | 2 | 3 | 1 | 2 |
| Concentration of acetone in aqueous alkali solution containing hydroperoxides (% by weight) | 0 | 0.1 | 0.99 | 2.91 | 0.09 |
| Retention percent (%) | | | | | |
| After 2-hour lapse of time | 99.9 | 96.5 | 97.5 | 93.0 | 48.3 |
| After 4-hour lapse of time | 97.9 | — | 92.4 | 75.0 | 0.97 |
| After 6-hour lapse of time | 96.8 | — | 86.7 | — | 0.76 |
| After 10-hour lapse of time | 94.9 | 91.0 | 77.7 | 44.3 | — |

TABLE 2

|  | Example | | Comparative Example |
| --- | --- | --- | --- |
|  | 4 | 5 | 3 |
| "A" value of aqueous sodium hydroxide solution used for extraction | 0 | 4.2 | 13.7 |
| Retention percent after 2-hour lapse of time (%) | 96.6 | 96.6 | 96.0 |

What is claimed is:

1. In a process for producing an object compound, which comprises the steps of:
   (i) subjecting a liquid material containing an aromatic hydrocarbon substituted with an alkyl group to oxidation thereby obtaining a liquid reaction mixture;
   (ii) extracting hydroperoxides in the liquid mixture with an aqueous alkali solution to obtain an extract-1;
   (iii) extracting at least one hydroperoxide in the extract-1 with an organic solvent to obtain an extract-2, wherein the aqueous solution separated after extracting in this step is recycled to the step (ii);
   (iv) subjecting the hydroperoxides in the extract-2 to acid decomposition, thereby obtaining a reaction mixture containing the object compound and acetone; and
   (v) distilling the reaction mixture to separate the object compound and the organic solvent, wherein the organic solvent is recycled to the step (iii),
   the process comprising separating acetone from the organic solvent separated in the step (v) so that the concentration of acetone contained in the extract-1 is kept to not more than 1% by weight.

2. The process according to claim 1, wherein the concentration of acetone contained in the extract-1 is not more than 0.1% by weight.

3. The process according to claim 1, wherein the aromatic hydrocarbon substituted with an alkyl group comprises 1,3-diisopropylbenzene.

4. In a process for producing an object compound, which comprises the steps of:
   (i) subjecting a liquid material containing an aromatic hydrocarbon substituted with an alkyl group to oxidation thereby obtaining a liquid reaction mixture;
   (ii) extracting hydroperoxides in the liquid mixture with an aqueous alkali solution to obtain an extract-1;
   (iii) extracting at least one hydroperoxide in the extract-1 with an organic solvent to obtain an extract-2, wherein the aqueous solution separated after extracting in this step is recycled to the step (ii);
   (iv) subjecting the hydroperoxides in the extract-2 to acid decomposition, thereby obtaining a reaction mixture containing the object compound and a by-produced acetone; and
   (v) distilling the reaction mixture to separate the object compound and the organic solvent, the organic solvent separated in this step is recycled to the step (iii),
   the process comprising controlling the A value of the aqueous alkali solution used in the step (ii) to not more than 10, wherein the A value is a volume in terms of ml of the below-defined aqueous hydrochloric acid solution consumed between a first inflection point and a second inflection point in a pH titration curve obtained when 10 ml of the aqueous alkali solution is subjected to titration with a 1 N aqueous hydrochloric acid solution, provided that when the inflection point is not clear, or when there are three or more inflection points, the A value is a volume in terms of ml of said aqueous hydrochloric acid solution consumed during a pH transition of from 7 to 2 in the above-defined titration.

5. The process according to claim 4, wherein the aqueous alkali solution has the A value of not more than 5.

6. The process according to claim 4, wherein the aromatic hydrocarbon substituted with an alkyl group comprises 1,3-diisopropylbenzene.

* * * * *